United States Patent [19]
Dos Santos et al.

[11] Patent Number: 5,905,168
[45] Date of Patent: May 18, 1999

[54] PROCESS FOR TREATING A MATERIAL COMPRISING A POLYMER BY HYDROLYSIS

[75] Inventors: Emmanuel Dos Santos, Feyzin; Pascal Mettvier, Sainte-Foy-les-Lyon; Michel Gubelmann, Paris, all of France

[73] Assignee: Rhone-Poulenc Chimie, Courbevoie Cedex, France

[21] Appl. No.: 08/454,215

[22] PCT Filed: Dec. 10, 1993

[86] PCT No.: PCT/FR93/01232

§ 371 Date: Jul. 23, 1995

§ 102(e) Date: Jul. 23, 1995

[87] PCT Pub. No.: WO94/13616

PCT Pub. Date: Jun. 23, 1994

[30] Foreign Application Priority Data

Dec. 11, 1992 [FR] France .................................. 92 15206

[51] Int. Cl.$^6$ ..................................................... C07C 55/00
[52] U.S. Cl. .......................... 562/590; 562/513; 562/523; 562/526
[58] Field of Search ...................................... 562/526, 523, 562/578, 590, 513; 502/325

[56] References Cited

FOREIGN PATENT DOCUMENTS

| 23813 | 4/1959 | German Dem. Rep. . |
| 867546 | 6/1952 | Germany . |
| 3016225 | 10/1981 | Germany . |

*Primary Examiner*—Michael L. Shippen
*Attorney, Agent, or Firm*—Burns, Doane, Swecker & Mathis, L.L.P.

[57] ABSTRACT

Process for the treatment of a material comprising a polymer, especially a polyamide. The process consists in subjecting the polyamide to hydrolysis in the presence of a hydrolyzing nitrous grouping and transforming the hydrolyzed compounds into diacids. The treatment of a polyamide 6.6 results in the recovery of adipic acid and other diacids corresponding to the participating acid monomer and to the transformation of at least one part of the diamine monomer into diacids.

23 Claims, No Drawings

PROCESS FOR TREATING A MATERIAL COMPRISING A POLYMER BY HYDROLYSIS

The present invention relates to a process for treating a material comprising a polymer to recover at least partially the monomers forming the polymer.

It relates more particularly to a process for treating a material comprising a polymer containing amide functional groups by oxidative hydrolysis of these amide functional groups to regenerate monomers which can be employed for the synthesis of identical or different polymers.

Synthetic materials and, among these, polymers containing amide functional groups, such as polyamides and more particularly polyamide 6.6 or polyamide 6 are increasingly employed for the production of varied articles such as textile fibres, technical industrial yarns, filaments or moulded articles such as components for electricity, electronics or motor vehicles. These synthetic materials are generally employed in the form of compositions containing various additives in addition to the synthetic material in order, for example, to increase their stability to heat or to radiations, to improve their mechanical, electrical or electrostatic properties, colorants and pigments. These additives are of very varied nature and may be organic as well as inorganic compounds.

In addition, especially in the case of the production of moulded articles, the compositions include fillers, frequently inorganic, such as glass fibres, talc, clay and the like.

The materials thus produced may be destroyed after use. One of the means for conventional destruction is incineration, which enables energy to be recovered. However, it is also proposed to recycle these materials. One of the means of recycling consists in depolymerizing the polymer or synthetic material into compounds of lower degree of condensation and, if possible, regenerating the initial monomers to enable them to be recycled into the polymerization processes. One of the processes proposed for recycling polyamide is a process consisting in hydrolysing the polymer in basic medium. However, this process does not make it possible to regenerate the monomers and generally requires a preliminary separation between the polymer and the fillers. Moreover, the additives present in the polymer, especially when they are organic in nature, may contaminate the products recovered after the hydrolysis, it being possible for this contamination to prevent their being recycled.

One of the objectives of the present invention is especially to propose a process making it possible to treat materials which may comprise fillers and/or additives, to hydrolyse the amide functional groups of the polymer present in the material in order to regenerate, on the one hand, the original dicarboxylic acid and, on the other hand, to produce one or more carboxylic acids whose chemical structure corresponds substantially to that of the original diamine or amino acid monomers.

To this end, the invention proposes a process for treating a material comprising a polymer containing at least amide functional groups. This process is characterized in that it consists in subjecting the material to a hydrolysis in the presence of nitrous groups dissolved in the hydrolysis medium and to an oxidation.

According to a preferred embodiment the hydrolysis medium is an oxidizing medium.

According to a characteristic of the invention the nitrous groups are obtained by chemical or thermal decomposition of at least one compound containing these groups.

Thus, compounds generating nitrous groups which may be mentioned by way of example are nitric acid, alkali metal and metal nitrites, nitrous vapours ($NO_x$) or the like.

The hydrolysis medium is an aqueous medium exhibiting an acid pH preferably lower than 1.

In a preferred embodiment the $H^+$ concentration in the medium is at least 1 mole/l (1N).

The process of the invention is advantageously carried out by maintaining the hydrolysis medium at a temperature lower than 100° C., preferably between 40 and 100° C. However, the process of the invention may be carried out under pressure at a temperature above 100° C., for example at a temperature of between 100 and 200° C.

The reaction period is determined so as to have a complete hydrolysis of the polymer and is, for example, a few hours (1 to 10 hours).

It may also be advantageous to have an atmosphere charged with nitrous vapours above the hydrolysis medium.

Solid residues are advantageously removed after reaction, especially by filtration.

The mixture may then be cooled and concentrated to allow the crystallization of the dicarboxylic acids formed. This method for recovering the carboxylic acids is the one most commonly employed, but the separation of these acids may be obtained by any appropriate process.

According to another embodiment the hydrolysis treatment of the invention is carried out in the presence of oxidation catalysts. Suitable catalysts are, for example, metal compounds such as copper, vanadium, titanium, iron, cobalt, molybdenum, nickel, ruthenium, manganese or iridium compounds or the like. Examples which may be mentioned are ammonium vanadate and copper nitrate.

The materials which can be treated by the process of the invention are all the materials comprising a polymeric synthetic material in which at least one repeat unit contains at least one amide functional group. Thus, the hydrolysis process of the invention makes it possible to cut the chains especially at each amide functional group to re-form at least the acidic functional group of the original monomer or oligomer and to convert the original diamine monomers or oligomers at least partially into compounds containing a dicarboxylic functional group.

The process of the invention applies more particularly to the treatment of polymers originating from at least one monomer containing acidic and/or amine functional groups which are not linked directly to an aromatic nucleus.

Other organic compounds present in the polymer or compounds not converted into dicarboxylic acids undergo an oxidation in the hydrolysis medium of the invention and are therefore generally degraded to carbon, $CO_2$, $H_2O$ and CO.

The polymeric synthetic materials that can be treated by the process of the invention are, for example, polyamides, polyetheresteramides, polyesteramides, polyetheramides and polyaramids.

This process is preferably applied to the treatment of polyamides such as the polyamides obtained by polycondensation of a linear dicarboxylic acid with a linear diamine, such as PA 6.6, PA 6.10, PA 6.12 or between an aromatic dicarboxylic acid and a linear or aromatic diamine, such as polyterephthatamides, polyisophthalamides, polyaramids and polyamides obtained by polycondensation of an amino acid with itself, it being possible for the amino acid to be generated by the opening of a lactam ring, such as, for example, PA 6, PA 7, PA 11, PA 12. The process of the invention is also suitable for treating the copolyamides derived especially from the above polyamides, or mixtures of polyamides or copolyamides.

The materials which can be treated by the process of the invention may also contain components other than the polymeric synthetic material. In fact, and this represents a considerable advantage of the process, it is not necessary to separate the polymeric synthetic material from the other components such as fillers, adjuvants or additives which are generally mixed with the said material to improve some of its properties, or to give it a different appearance, as in the case of colorants.

Thus, the generally inorganic fillers which are mixed with the synthetic material, especially to reinforce its mechanical properties, are not hydrolysed and precipitate in the hydrolysis medium. The same goes for the inorganic additives such as titanium oxide, usually employed as delustring agent in textile or technical yarns and fibres.

The other organic additives are generally hydrolysed, oxidized and converted into carbon, carbon monoxide, water or other oxides. However, it is also possible for the degradation of some of these compounds not to be complete, but the resulting degradation products will be separated form the dicarboxylic acids by crystallization of the latter.

Thus, the process of the invention makes it possible to treat the raw materials from their recovery, such as, for example, carpet yarns, nylon stockings and moulded articles. The materials can be treated as they are or after a treatment such as separation of other materials like metal inserts, or reduction to small particles, for example by grinding or chopping to permit an accelerated hydrolysis.

The process of the invention therefore permits a recycling of polymers such as polyamides in the form of diacid monomers. In the case of the treatment of PA 6.6 the process makes it possible to recover the adipic acid originally introduced and to convert hexamethylenediamine at least partially to adipic acid or dicarboxylic acids containing a smaller number of carbon atoms, such as, for example, glutaric acid and succinic acid.

Other objectives, advantages and characteristics of the invention will appear more clearly in the light of the examples given below solely by way of guidance.

In a preferred embodiment, the process of the invention is carried out in a reactor containing a hydrolysis medium consisting generally of an aqueous solution of nitric acid, to which sodium nitrite—as a compound generating nitrous groups—and, optionally, catalysts are added.

The material to be treated is added to the hydrolysis medium as it is or in chopped or ground form. In most cases the material is introduced as it is.

The reaction mixture is kept stirred and at a determined temperature for approximately 4 hours.

After reaction the reaction mixture is cooled and diluted with water.

The quantity of dicarboxylic acid, especially of adipic, glutaric and succinic acid when the original polymer is PA 6.6 or PA 6, is determined by measurement using liquid phase chromatography.

The efficiency of conversion to dicarboxylic acids is expressed by the ratio of the measured quantity of acids in relation to the theoretical quantity of acids which is obtained, assuming that the hydrolysis of the amide functional group regenerates the original acidic functional groups and converts the amine functional groups to acid functional groups.

The reaction mixture is optionally filtered to remove the solid residues, and the dicarboxylic acids are then separated and recovered by concentration and crystallization, using known techniques for the crystallization of adipic acid.

EXAMPLE 1

Material treated: pure polyamide 6.6 containing:

730 meq./kg $NH_2$ and
750 meq./kg COOH.

This polymer has a degree of polymerization DP close to 12.

The hydrolysis medium contains 5 ml of nitric acid solution at a concentration of 56% by weight with 76.8 mg of CuO and 4.5 mg of $NH_4VO_3$.

17.1 mg of $NaNO_2$ are added to the mixture.

A considerable release of nitrous vapour takes place in the reactor.

0.3265 g of PA 6.6 are then added and the mixture is kept at 70° C. for 4 hours. (This mass of PA 6.6 potentially contains 1832 meq. of COOH functional groups per kg of PA and 1832 meq. of $NH_2$ functional groups per kg of PA).

After cooling and dilution with water, the dicarboxylic acids produced are determined by liquid phase chromatography:

adipic acid: 1.081 mol/kg
glutaric acid: 0.021 mol/kg
succinic acid: 0.101 mol/kg
theoretical quantity of regenerated diacids: 1.832 mol/kg
conversion yields
   adipic acid: 59.0%
   glutaric acid: 1.1%
   succinic acid: 5.5%
   total diacids: 65.6%

EXAMPLES 2 TO 6 AND COMPARATIVE EXAMPLES A AND B

The results obtained in the treatment of pure PA 6.6 with various operating conditions are collated in Table I below.

TABLE I

| test | 1 | 2 | 3 | 4 | 5 | 6 | A | B |
|---|---|---|---|---|---|---|---|---|
| PA 6.6 | | | | | | | | |
| no. mmol AA (1) | 1.39 | 1.430 | 1.43 | 1.42 | 1.41 | 1.40 | 1.40 | 1.41 |
| no. mmol HMDA (1) | 1.39 | 1.43 | 1.43 | 1.42 | 1.41 | 1.40 | 1.40 | 1.41 |
| free residual AA (mmol) | 0.333 | 0.341 | 0.341 | 0.340 | 0.337 | 0.334 | 0.334 | 0.337 |
| $NaNO_2$ | 0.313 | 0.338 | 1.414 | 0.304 | 0.32 | 5.38 | ... | ... |
| Acid | $HNO_3$ 56% | $HNO_3$ 56% | $HNO_3$ 56% | $HNO_3$ 29% | $HNO_3$ 56% | $HNO_3$ 56% | $HNO_3$ (bleached) 56% | $H_2SO_4$ 36.3% |
| Catalyst | $Cu(NO_3)_2$ | $NH_4VO_3$ | ... | $Cu(NO_3)_2$ | $Cu(NO_3)_2$ | ... | ... | $Cu(NO_3)_2$ |
| Temperature | 70° C. | 70° C. | 70° C. | 70° C. | 70° C. | 70° C. | 70° C. | 70° C. |
| Duration | 4 h | 4 h | 4 h | 4 h | 4 h | 4 h | 4 h | 4 h |

TABLE I-continued

| test | 1 | 2 | 3 | 4 | 5 | 6 | A | B |
|---|---|---|---|---|---|---|---|---|
| Theretical mmol diacid | 2.120 | 2.17 | 2.17 | 2.16 | 2.15 | 2.13 | 2.13 | 2.15 |
| mmol SA | 0.140 | 0.155 | 0.109 | 0 | 0.102 | 0.179 | 0 | 0 |
| Y % | 6.62 | 7.12 | 5.03 |  | 4.75 | 8.42 |  |  |
| mmol GA | 0.017 | 0.022 | 0 | 0 | 0 | 0.038 | 0 | 0 |
| Y % | 0.80 | 1.01 |  |  |  | 0.81 |  |  |
| mmol AA | 1.082 | 1.110 | 1.099 | 0.496 | 1.06 | 1.136 | 0.008 | 0.024 |
| Y % | 51.19 | 50.96 | 50.69 | 23 | 49.54 | 53.42 | 0.38 | 1.11 |
| mmol diacids | 1.239 | 1.287 | 1.208 | 0.496 | 1.16 | 1.353 | 0.008 | 0.024 |
| Y % | 58.62 | 59.09 | 53.72 | 23 | 54.29 | 63.63 | 0.38 | 1.11 |

AA = adipic acid
GA = glutaric acid
SA = succinic acid
HMDA = hexamethylenediamine
(1) no. of mmol of monomers used to produce the polymer These examples clearly show that the presence of nitrous groups is necessary to obtain a hydrolysis of the amide functional group (Example A employs a nitric acid bleached with sulphonic acid to remove the nitrous groups).

Furthermore, they clearly show that the process of the invention makes it possible, on the one hand, to regenerate a large proportion of the original acidic monomer, but also to convert a considerable proportion of the amide monomer to diacidic compounds.

EXAMPLES 7 AND 8

These examples are related to the treatment of different polymers:
Example 7: pure polyamide 6.6 (in the absence of free monomers
Example 8: pure polyamide 6.

The operating conditions and the results are collated in Table II.

TABLE II

| test | 7 | 8 |
|---|---|---|
| Polymer | Pure PA 6.6 | Pure PA 6 |
| no. mmol A (1) | 1.341 | . . . |
| no. mmol HMDA (1) | 1.341 | . . . |
| no. mmol caprolactam (1) | . . . | 3.15 |
| NaNO$_2$ | 0.338 | 0.338 |
| Acid | HNO$_3$ 56% | HNO$_3$ 56% |
| Catalyst | Cu(NO$_3$)$_2$ NH$_4$VO$_3$ | Cu(NO$_3$)$_2$ NH$_4$VO$_3$ |
| Temperature | 70° C. | 70° C. |
| Duration | 4 h 40 | 4 h 35 |
| Theoretical mmol diacid | 2.68 | 3.15 |
| mmol SA | 0.388 | 0.968 |
| Y % | 12.48 | 30.68 |
| mmol GA | 0.058 | 1.452 |
| Y % | 1.87 | 46.02 |
| mmol AA | 1.517 | 0.189 |
| Y % | 48.78 | 5.99 |
| mmol diacids | 1.963 | 2.609 |
| Y % | 63.12 | 82.70 |

(1) no. of mmol of monomers used to produce the polymer

EXAMPLE 9

The process described in Example 1 is reproduced, but with the polyamide 6.6 being replaced with a stocking fabric made of nylon PA 6.6.

After treatment, the efficiency of conversion of the polyamide to diacid is expressed as the weight of diacids recovered per kg of stocking:

adipic acid: 705 g/kg glutaric acid: 2.4 g/kg succinic acid: 129 g/kg total diacids: 758 g/kg Efficiency of conversion: 75.8%.

EXAMPLE 10

The material treated is a moulded article produced from a composition made of PA 6.6 and PA 6 filled with a talc-type inorganic filler and containing conventional additives for heat stabilization, such as CuI/KI.

This article was introduced into a hydrolysis medium consisting of a solution of nitric acid at a concentration of 56% by weight, to which copper nitrate, ammonium vanadate and sodium nitrite were added.

The mixture was kept at 70° C. for 4 hours.

After cooling the mixture was diluted by adding water.

The mixture contains insoluble compounds of whitish colour, which are removed by filtration.

The quantity of diacids in the hydrolysis mixture which are recovered after filtration is determined by liquid phase chromatography.
The results obtained are:

adipic acid: 1.562 mmol glutaric acid: 0.336 mmol succinic acid: 0.562 mmol total diacids: 2.460 mmol The efficiencies of conversion of polyamide used to diacids are:
polyamide used PA 6.6: 4.13 mol/kg of composition PA 6: 1.33 mol/kg of composition diacids formed adipic acid: 2.20 mol/kg of composition glutaric acid: 0.47 mol/kg of composition succinic acid: 0.79 mol/kg of composition total acids: 3.46 mol/kg of composition.

The efficiency of conversion of the polyamides to diacids is 63.4%. These diacids are subsequently recovered by crystallization.

Thus, crystalline adipic acid is recovered in a high degree of purity (higher than 95%) by cooling the filtered hydrolysis mixture.

The other diacids can also be recovered after crystallization of the adipic acid and concentration of the mixture.

We claim:

1. A process for treating a material comprising a polymer containing an amide functional group, said process comprising hydrolyzing said material in the presence of nitrous groups dissolved in a hydrolysis medium to obtain a hydrolyzed material and oxidizing said hydrolyzed material;
wherein said polymer comprises a polyamide obtained by the polycondensation of a diamine with a diacid.

2. The process according to claim 1, wherein the hydrolysis medium is an oxidizing medium.

3. The process according to claim 1, wherein the nitrous groups are obtained by the thermal or chemical decomposition of at least one compound containing $NO_x$ groups.

4. The process according to claim 3, wherein the at least one compound containing $NO_x$ groups is nitric acid, an alkali metal nitrite, a metal nitrite or nitrous vapors.

5. The process according to claim 1, wherein the hydrolysis medium is an aqueous solution with a pH lower than 1.

6. The process according to claim 5, wherein the hydrolysis medium has an $H^+$ concentration of at least 1 mole/l.

7. The process according to claim 1, wherein the hydrolyzing is carried out at a temperature of 100° C. or lower.

8. The process according to claim 1, wherein the hydrolyzing is carried out at a temperature between 40 and 100° C.

9. The process according to claim 1, wherein the hydrolyzing occurs in the presence of an oxidation catalyst.

10. The process according to claim 9, wherein the oxidation catalyst is a metal compound.

11. The process according to claim 10, wherein the metal compound is a compound of copper, vanadium, titanium, iron, cobalt, molybdenum, nickel, ruthenium, manganese or iridium.

12. The process according to claim 1, wherein after hydrolyzing, the solid residues are removed from the hydrolysis mixture, and the dicarboxylic acids produced are extracted from the hydrolysis mixture.

13. The process according to claim 12, wherein the dicarboxylic acids are extracted by crystallization.

14. The process according to claim 13, wherein the dicarboxylic acids are dicarboxylic acid compounds having a number of carbon atoms equal to or less than the number of carbon atoms in the monomer compound or compounds employed to synthesize the polymer.

15. The process according to claim 1, wherein the polymer is a polymer originating from at least one monomer containing at least one acidic and/or amine functional group not bonded directly to an aromatic nucleus.

16. The process according to claim 15, where in the polymer is selected from the group consisting of polyamides, polyether amides, polyester amides, polyether ester amides, polyaramids, copolymers thereof and mixtures thereof.

17. The process according to claim 16, wherein the polyamides are selected from the group consisting of polyamides obtained by the polycondensation of a diamine with a diacid, polyamides obtained by polycondensation of an amino acid, the copolyamides thereof and mixtures thereof.

18. The process according to claim 17, wherein the polyamides are selected from the group consisting of PA 6.6, PA 6.4, PA 6.11, PA 6.12, A 4.6, PA 6, PA 12 and PA 11.

19. The process according to claim 1, wherein the material comprises a polymer or a mixture of polymers.

20. The process according to claim 1, wherein the material further comprises additives and inorganic or organic fillers.

21. The process according to claim 1, wherein the material is hydrolyzed without pretreatment.

22. The process according to claim 1, wherein the material is treated to reduce the particle size or to separate the material from other materials prior to the hydrolyzing.

23. A process for treating a polymer containing amide functional groups made by the polycondensation of a dicarboxylic acid with a diamine, said process comprising treating the polymer with a hydrolysis medium having nitrous groups dissolved therein, wherein said treating generates the original dicarboxylic acid, and the original diamine, and converts a portion of the original diamine into a dicarboxylic acid.

* * * * *